(12) United States Patent
Pai et al.

(10) Patent No.: US 7,273,619 B2
(45) Date of Patent: Sep. 25, 2007

(54) TRANSDERMAL COMPOSITION OF AN ANTIVOMITING AGENT

(75) Inventors: Chaul Min Pai, Daejeon (KR); Jin Deog Song, Daejeon (KR); Joong Woong Cho, Daejeon (KR)

(73) Assignee: Samyang Corporation, Seoul (KR)

( * ) Notice: Subject to any disclaimer, the term of this patent is extended or adjusted under 35 U.S.C. 154(b) by 551 days.

(21) Appl. No.: 10/414,827

(22) Filed: Apr. 15, 2003

(65) Prior Publication Data

US 2004/0022835 A1 Feb. 5, 2004

Related U.S. Application Data

(63) Continuation-in-part of application No. 09/913,085, filed on Jan. 17, 2002, now abandoned.

(51) Int. Cl.
*A61F 13/00* (2006.01)
*A61F 15/16* (2006.01)

(52) U.S. Cl. .................................. 424/449; 424/448

(58) Field of Classification Search ......... 424/448–449
See application file for complete search history.

(56) References Cited

U.S. PATENT DOCUMENTS 5,364,628 A * 11/1994 Kissel et al. ................. 424/448
5,456,745 A * 10/1995 Roreger et al. .......... 106/140.1
5,626,866 A * 5/1997 Ebert et al. ................. 424/447
5,840,336 A * 11/1998 Hsu et al. .................... 424/484
5,922,341 A * 7/1999 Smith et al. ................ 424/430

* cited by examiner

*Primary Examiner*—Michael G. Hartley
*Assistant Examiner*—Micah-Paul Young
(74) *Attorney, Agent, or Firm*—Thorpe North & Western LLP

(57) ABSTRACT

The present invention relates to a transdermal composition of an antivomiting agent, and more particularly to a transdermal composition of an antivomiting agent which can minimize skin irritation by employing tropisetron as the antivomiting agent as well as by adjusting its pH to be in the range of 8 to 9 thus enhancing its rate of skin penetration thereby reducing the amount of a skin penetration enhancer used.

22 Claims, No Drawings

TRANSDERMAL COMPOSITION OF AN ANTIVOMITING AGENT

This application is a continuation in part of U.S. application Ser. No. 09/913,085 filed on Jan. 17, 2002, now abandoned which is based on PCT/KR 00/00096 filed on Feb. 9, 2000 with a priority filing date of Feb. 9, 1999. This application also claims the benefit of the priority filing date of Korean patent application No. 02-79659 filed on Dec. 13, 2002.

BACKGROUND OF THE INVENTION

Field of the Invention

The present invention relates to a transdermal composition of an antivomiting agent, and more particularly to a transdermal composition of the antivomiting agent tropisetron.

Most patients undergoing anticancer treatment suffer from side effects of the treatment such as nausea and vomiting, which are the most common complaints by patients. To prevent or minimize these side effects of anticancer treatments, antagonists for 5-hydroxytryptamine subtype 3 (hereinafter referred to as 'serotonin') such as tropisetron, ondansetron, granisetron and dolasetron, known as serotonin receptor antagonists, have been widely administered, either parenterally or orally, on a daily basis.

However, as most anticancer drugs have been developed in the form of injections, the administration of an antivomiting agent via injection in combination with the anticancer drugs would appear to aggravate the pain experienced by the patient and seems inappropriate for home use. In addition, the oral administration of an antivomiting agent has the drawback in that it cannot be administered to patients experiencing the side effect of severe vomiting. Moreover, there is a problem in that the blood level of the antivomiting agent tends to rise to a level of toxicity and then rapidly decrease when the composition is administered either parenterally or orally.

To cope with these problems, there has been an attempt to formulate a composition of an antivomiting agent in the form of patches so that the antivomiting agent can be administered transdermally.

However, attempts to transdermally administer antivomiting agents has raised other problems. For example, penetration enhancers commonly used in transdermal compositions, such as fatty acid derivatives (e.g., terpenes and glycerol monolaurate), induce skin irritation. In addition, when a transdermal composition with a low viscosity is used, the blood level of the drug may easily drop below the effective level thus lessening the desired pharmacological effect.

For transdermal administration, it is essential to maintain an effective level of the antivomiting agent in the blood stream so that it can serve its function as effectively as if it were administered by injection. Therefore, the dosage needed for transdermal administration would be higher than in other formulations due to limitations in the amount and rate of the antivomiting agent absorbed. In this respect, ondansetron is not suitable for a transdermal formulation since the dose for transdermal administration is much higher than the dose needed for efficacious oral or parenteral administration(24 to 32 mg per day). In contrast, tropisetron, when administered orally or parenterally, can exhibit efficacy even at a dose of 5 mg/day, thus requiring only 30 mg/day for efficacious transdermal administration. Therefore, tropisetron appears more suitable for a transdermal formulation.

U.S. Pat. No. 6,019,997, which relates to a composition useful for the transdermal delivery of a drug, discloses a transdermal system comprising a drug dissolved in a lower alcohol, water and at least two emulsifiers, with a viscosity of more than 4,000 centipoises at room temperature, which can allow a drug to penetrate through the skin in the absence of an auxiliary thickener. However, the composition disclosed in the above U.S. patent has the following drawbacks: (i) the emulsifier system uses an emulsifier having such a special structure as to be sufficiently viscous in the absence of an auxiliary thickener, (ii) because a solid emulsifier must be used as at least one of the emulsifiers, the composition forms a suspension, in which a solid is dispersed in liquid solution, having too high a viscosity and reduced safety, and (iii) no method of minimizing skin irritation is taught.

European Pat. No. 0682942 relates to a composition for external use for delivery through the skin of a physiologically active substance comprising antivomiting agents such as ondansetron and granisetron. The above patent provides a system which can enhance the absorption of the physiologically active substance through skin and also decrease skin irritation by way of dissolving a physiologically active substance in a mixed solution consisting of an alcohol and a buffer solution as well as using a monoterpene as a skin penetration enhancer along with a nonionic surfactant. However, the above European patent has the following drawbacks: (i) the monoterpene used therein as a skin penetration enhancer is highly irritating to the skin and the skin penetration rate thereof is relatively low as well, (ii) the patent does not disclose any method for increasing the viscosity of the composition into a suitable range, which is an important property for transdermal drug delivery compostions.

International Publication No. WO 00/47208 relates to a transdermal composition of an antivomiting agent, and more particularly to a transdermal composition of an antivomiting agent comprising: (i) a lower alcohol and water as a solvent, (ii) fatty acid derivatives and amide compounds as skin penetration enhancers, (ii) tropisetron, ondansetron, granisetron or a mixture thereof as the antivomiting agent. However, the above-mentioned invention also has problems in that there was no disclosure relating to enhancing the skin penetration rate by adjusting the pH of the transdermal composition containing an antivomiting agent.

SUMMARY OF THE INVENTION

It has been widely recognized that it would be advantageous to develop a transdermal composition of an antivomiting agent which minimizes skin irritation and has an enhanced skin penetration rate which maintains an effective level of the drug in the blood stream.

The present invention provides a composition which can enhance the rate of skin penetration of a drug as well as minimize skin irritation by way of (i) using, as an antivomiting agent, tropisetron, which is efficacious in acute vomiting induced by chemotherapic agents such as cisplatin, and is suitable for a transdermal formulation as well, even at a low concentration, and (ii) adjusting the pH of the composition thereby improving the skin penetration rate of tropisetron thereby requiring use of minimal amounts of tropisetron hydrochloride salt and glycerol monolaurate, which are the main causes of skin irritation.

In accordance with more detailed aspects of the present invention, the transdermal composition of an antivomiting agent comprises:(a) a vehicle for transdermal delivery comprising (i) 25 to 45 wt % of a mixed solution comprising ethanol and propylene glycol, (ii) a skin penetration enhancer containing 0.5 to 1.5 wt % of a fatty acid ester, 2 to 5 wt % of an amide compound; (iii) 50 to 70 wt % of a buffer solution; and (b) 2 to 4 wt % of tropisetron, based on the weight of the tropisetron vehicle, wherein the pH of said composition is within the range of 8 to 9.

The present invention also provides a method of transdermally delivering an antivomiting agent to a warm blooded animal comprising administering a transdermal delivery device containing the composition of the present invention.

Additional features and advantages of the invention will be apparent from the detailed description which follows, taken in conjunction with the accompanying examples which together illustrate, features of the invention.

DETAILED DESCRIPTION

Reference will now be made to the exemplary embodiments illustrated in the examples, and specific language will be used herein to describe the same. It will nevertheless be understood that no limitation of the scope of the invention is thereby intended. Alterations and further modifications of the inventive features illustrated herein, and additional applications of the principles of the inventions as illustrated herein, which would occur to one skilled in the relevant art and having possession of this disclosure, are to be considered within the scope of the invention.

It must be noted that, as used in this specification and the appended claims, the singular forms "a," "an," and "the" include plural referents unless the context clearly dictates otherwise. Thus, for example, reference to a polymer containing "a terminal group" includes reference to two or more such groups, and reference to "a hydrophobic drug" includes reference to two or more of such drugs.

The present invention relates to a transdermal composition of an antivomiting agent for treatment as well as prevention of nausea or vomiting induced during anticancer treatment which comprises (a) a vehicle for transdermal delivery and (b) an antivomiting agent.

Tropisetron, which is used in the present invention as the antivomiting agent, is a selective serotonin (i.e. 5-hydroxytriptamine subtype 3) receptor antagonist and is very effective in preventing acute vomiting induced by administration of a chemotherapeutic agent, such as cisplatin. It is preferable to use tropisetron in the form of a pharmaceutically acceptable salt thereof, more preferably as the tropisetron hydrochloride salt.

Tropisetron is used as an antivomiting agent in an amount of 2 to 4 wt %, more preferably 2.5 to 3.5 wt % based on the weight of the vehicle, so as to exhibit the desired skin penetration rate with minimal skin irritation. If the amount of antivomiting agent is less than 2 wt %, the transdermal composition does not show substantial efficacy. In contrast, if the amount exceeds 4 wt % the skin penetration rate increases, and in turn, skin irritation increases as well.

Moreover, the vehicle of the present invention comprises a solvent for enhancing the solubility of the drug and the intercellular fluidity, a fatty acid ester which acts on the lipids of the keratotic skin layer thus enhancing lipid solubility and intercellular fluidity thereby promoting distribution of the drug into the lipid layer, and skin penetration enhancers such as amide compounds, and a buffer solution as a base vehicle.

The mixed solvent which is used in the present invention comprises ethanol as the main solvent and propylene glycol as an auxiliary solvent. Ethanol reversibly changes the structure of the keratin layer of the skin by extracting polar lipids therefrom, thereby promoting skin penetration of the antivomiting agent, and it also plays a role in dissolving the antivomiting agent and the penetration enhancers which have low solubility in the water-soluble vehicle. Moreover, propylene glycol, when used in combination with a fatty acid ester, synergistically promotes the skin penetration of the antivomiting agent.

Tropisetron is used as the antivomiting agent in an amount of 2 to 4 wt %, more preferably 2.5 to 3.5 wt % based on the weight of the vehicle. Ethanol is used in the amount of 15 to 25 wt %, more preferably 18 to 22 wt %, with reference to 100 wt % of the vehicle. Furthermore, it is preferable that the solution comprise propylene glycol in an amount of 10 to 20 wt %, more preferably 14 to 16 wt %, with reference to 100 wt % of the vehicle.

There is a synergistic increase in the skin penetration rate when a fatty acid ester and amide compound are used in combination as skin penetration enhancers for enhancing the drug solubility in the keratin layer thereby promoting distribution into the skin.

The fatty acid ester which is used in the present invention is selected from the group consisting of glycerol monolaurate, glycerol monooleate, glycerol monolinoleate, glycerol trilaurate, glycerol trioleate, glycerol tricaprylate, propylene glycol monolaurate, propylene glycol dilaurate, caprylic/capric triglyceride, methyl laurate, methyl caprate, isopropyl myristate, isopropyl palmitate, ethyl oleate and oleyl oleate. Among these, glycerol monolaurate is most preferred. The fatty acid ester of the present invention is used in the amount of 0.5 to 1.5 wt %, preferably 1 to 1.5 wt %. If the amount of the fatty acid ester is less than 0.5 wt %, the desired skin penetration rate cannot be achieved. In contrast, if the amount exceeds 1.5 wt %, there is a problem with increased skin irritation.

The amide compound which is used in the present invention is selected from the group consisting of N,N-diethyl-m-toluamide, lauric acid diethanolamide, urea, dimethylformamide and dimethylacetamide, and among these, N,N-diethyl-m-toluamide is most preferred. It is preferable that the vehicle contains the amide compound in the amount of 2 to 5 wt %, preferably 2 to 4 wt %. If the amount of the fatty acid amide is less than 2 wt %, the desired skin penetration rate cannot be achieved. In contrast, if the amount exceeds 5 wt %, there is a problem with increased skin irritation.

The buffer solution which is used in the present invention is selected from the group consisting of a borate buffer solution, a phosphate buffer solution, a sodium bicarbonate buffer solution, and a glycine buffer solution.

The pH of the buffer solution used in the present invention is not specifically limited but is acceptable as long as the pH of the transdermal composition falls within the range of 8 to 9. The buffer solution is used in such an amount as to bring the final composition to 100 wt % and is preferably in the amount of 50 to 70 wt % with reference to 100 wt % of the vehicle.

It is preferable that the pH of the transdermal composition herein ranges from 8 to 9, more preferably from 8 to 8.5, since the skin penetration rate is enhanced within this pH range. The possible reasons for the enhanced skin penetration rate of the present invention is that the antivomiting agent, tropisetron, is used in a form of its hydrochloride salt which has a high solubility in the transdermal composition and the higher pH provides a stronger driving force for skin penetration. When the pH is less than 8, there is a problem with a resulting decrease in skin penetration. However, when the pH is greater than 9, there is a problem with decreased stability and the drug can easily be precipitated at varying temperatures.

The transdermal composition of the present invention may further comprise a thickener for preventing the composition from running down and out of the patch. It may be necessary to use a thickener when the transdermal composition is formulated into a reservoir patch.

However, in the case of employing a thickener, it is important to choose a suitable one since it may reduce the rate of skin penetration. Hydroxypropyl cellulose can be used, as a thickener herein, which is a cellulose with a weight average molecular weight ranging from 50,000 to 1,250,000, having a partially substituted poly(hydroxypropyl) ether and in addition may further comprise more than 0.6% of silica or other suitable anticaking agents. When considering the rate of skin penetration of the drug, the stability of the composition of the present invention and the process of preparing a formulation for transdermal administration, it is preferable to use a hydroxypropyl cellulose with a weight average molecular weight of 800,000 to 1,000,000 in an amount of 4 to 5 wt % with reference to 100 wt % of the vehicle.

The preferred dose of the composition of the present invention to be administered depends on the physical condition and body weight of the test subject, the form of the inventive composition, and the route and term of administration. In general, the preferred daily dose for an adult is 0.05 to 0.1 mg/kg.

As explained above, the less skin-irritating transdermal composition of an antivomiting agent as described herein may be prepared in a formulation for transdermal administration, such as a patch. A monolith vehicle patch, preferably a reservoir patch, may be employed in the present invention.

The present invention adjusts the pH of the composition to be within the range of 8 to 9 thus enhancing the skin penetration rate of tropisetron and lowering the dose of skin irritating skin penetration agents or drug needed.

The following examples will enable those skilled in the art to more clearly understand how to practice the present invention. It is to be understood that, while the invention has been described in conjunction with the preferred specific embodiments thereof, that which follows is intended to illustrate and not limit the scope of the invention. Other aspects of the invention will be apparent to those skilled in the art to which the invention pertains.

REFERENCE EXAMPLE 1

Determining Skin Penetration Rate

The skin penetration rate of the transdermal composition of an antivomiting agent herein was measured as follows:

A piece of cadaver skin was placed in a compartment between a donor and a receptor side such that the keratin layer of the skin faced the donor-side compartment. The effective area of skin exposed to the receptor solution was 0.636 cm². The receptor was filled with 5 ml of distilled water (receptor solution) and stirred at 600 rpm using a magnetic bar while the temperature was maintained at 32±0.5° C. using a thermostat with a circulatory pump. The donor compartment was filled with a degassed transdermal composition and a formulation to be tested and then sealed. Samples of the receptor solution were taken at 4, 8, 12, 21, 24 hours during the course of the experiment, followed by liquid chromatography using a μ-Bondapak C18 (5 μm, 30×0.46 cm) column. For the above liquid chromatography, a solution mixed with 0.01 M of a potassium phosphate solution (pH 4.0) and acetonitrile in a ratio of 4:6 was used as the developing solvent and the samples were analyzed using a UV detector at a wavelength of 284 nm.

The skin penetration rate was determined by the amount of antivomiting agent which penetrated per unit area of the skin per unit time, according to formula (I):

$$J_s = \frac{1}{A}\left(\frac{dQ}{dt}\right)_{ss} \quad (I)$$

wherein $J_s$ represents the penetration rate of the drug at a steady state, A represents the skin area, and $(dQ/dt)_{ss}$ means an amount (μg/h) of the drug penetrated per unit time at a steady state.

REFERENCE EXAMPLE 2

Determining the Degree of Skin Irritation

The degree of skin irritation of the transdermal composition herein was determined as follows:

Patch samples with and without the transdermal compositions were prepared. The skin surface of the test animal's backbone were carefully shaved 24 hours before testing. Each animal was prepared with two parts of abraded skin and two parts of intact skin. Then, two patch samples with the transdermal compositions were applied, one to an abraded area and one to intact skin parts, respectively. Two patch samples without the transdermal compositions were applied, one to an abraded area and one to intact skin.

The skin irritation was evaluated by the Toxicity Test Method and is numerically presented according to the widely employed Draiz method.

TABLE 1

| Degree of skin irritation (P.I.I.) | Type of skin irritation |
|---|---|
| <2 | Mild irritation |
| 2-5 | Moderate irritation |
| >5 | Severe irritation |

After applying the patches to the skin of the animals for 24 hours, the results of irritation such as erythema or edema were evaluated and given an individual Primary Irritation Index (P. I. I.). As shown in TABLE 1, the patches were categorized into three groups according to the degree of skin irritation (P. I. I.), and only the transdermal compositions with a P. I. I. range below 2 were suitable for transdermal administration.

EXAMPLES 1-2 AND COMPARATIVE EXAMPLES 1-2

A transdermal composition of an antivomiting agent comprising such ingredients as shown in TABLE 2, was formed by dissolving the tropisetron hydrochloride salt in a mixed solution consisting of anhydrous ethanol, propylene glycol, a borate buffer solution, glycerol monolaurate, diethyl toluamide followed by further addition of hydroxypropyl cellulose ($M_w$ 1,000,000) and then totally dissolving it in the mixture solution. The borate buffer solution was prepared by adding 0.2 M of sodium hydroxide to a solution admixed with 0.2 M of borate and 0.2 M of potassium chloride.

In TABLE 2 are shown the skin penetration rates of the prepared transdermal compositions determined using cadaver skin as mentioned above and the Primary Irritation Indices (P.I.I.) determined by the degree of skin irritation caused by the transdermal compositions.

TABLE 2

| Classification | Examples | | Comparative Examples | |
|---|---|---|---|---|
| | 1 | 2 | 1 | 2 |
| Antivomiting agent* (wt %) Tropisetron hydrochloride salt | 3 | 3 | 3 | 3 |
| Ingredients of vehicle (wt %) | | | | |
| Ethanol | 20 | 20 | 20 | 20 |
| Propylene glycol | 15 | 15 | 15 | 15 |
| Borate buffer solution (pH 8.0) | — | — | 61 | — |
| Borate buffer solution (pH 9.0) | — | — | — | 61 |
| Borate buffer solution (pH 10.0) | 61 | 61 | — | — |
| Glycerol monolaurate | 1 | 1 | 1 | 1 |
| Diethyl toluamide | 3 | 3 | 3 | 3 |
| Hydroxypropyl cellulose* | — | 4.3 | 4.3 | 4.3 |
| pH of transdermal composition | 8.2 | 8.2 | 6.2 | 7.7 |
| Skin penetration rate of antivomiting agent (µg/cm2/h) | 56.4 | 54.6 | 32.8 | 44.7 |
| Degree of skin irritation (P.I.I.) | — | 0.4 | 0.3 | 0.4 |

*wt % with reference to 100 wt % of the vehicle

As shown in TABLE 2, the transdermal compositions of the present invention employing borate buffer solutions with pH values ranging from 8 to 9 showed superior skin penetration rates and a low degree of skin irritation. Moreover, the skin penetration rate increased with an increase in the pH of the borate buffer solution. However, when the pH was higher than 11, the skin penetration rate was lowered to 30 µg/cm2/h, due to the precipitation of tropisetron induced by a decrease in solubility of the drug.

EXAMPLE 3 AND COMPARATIVE EXAMPLE 3

A transdermal composition of an antivomiting agent comprising such ingredients as shown in TABLE 3 was made by dissolving the tropisetron hydrochloride salt in a mixed solution consisting of anhydrous ethanol for pharmacopoeia, propylene glycol, a glycine buffer solution, glycerol monolaurate, diethyl toluamide followed by further addition of hydroxypropyl cellulose ($M_w$ 1,000,000) and then dissolving it in the mixture solution. The glycine buffer solution was prepared by using 0.2 M of glycine and 0.2 M of sodium hydroxide.

In TABLE 3 are shown the skin penetration rates of the prepared transdermal compositions determined using cadaver skin as mentioned above and the Primary Irritation Indices (P.I.I.) determined by the degree of skin irritation caused by the transdermal compositions.

TABLE 3

| Classification | Example 3 | Comparative Example 3 |
|---|---|---|
| Antivomiting agent* (wt %) Tropisetron hydrochloride salt | 3 | 3 |
| Ingredients of vehicle (wt %) | | |
| Ethanol | 20 | 20 |
| Propylene glycol | 15 | 15 |
| Glycine buffer solution (pH 8.6) | — | 61 |
| Glycine buffer solution (pH 10.0) | 61 | — |
| Glycerol monolaurate | 1 | 1 |
| Diethyl toluamide | 3 | 3 |
| Hydroxypropyl cellulose* | 4.3 | 4.3 |
| pH of transdermal composition | 8.4 | 7.3 |
| Skin penetration rate of antivomiting agent (µg/cm$^2$/h) | 56.8 | 30.2 |
| Degree of skin irritation (P.I.I.) | 1.0 | 0.8 |

*wt % with reference to 100 wt % of the vehicle

As shown in TABLE 3, the transdermal compositions of the present invention employing a glycine buffer solution with a pH ranging from 8 to 9 showed superior skin penetration rates and a low degree of skin irritation. Moreover, the skin penetration rate increased with increases in the pH of the glycine buffer solution.

EXAMPLES 4-5 AND COMPARATIVE EXAMPLE 4

A transdermal composition of an antivomiting agent comprising such ingredients as shown in TABLE 4 was made by dissolving the tropisetron hydrochloride salt in a mixed solution consisting of anhydrous ethanol, propylene glycol, a sodium bicarbonate buffer solution, glycerol monolaurate, diethyl toluamide followed by further addition of hydroxypropyl cellulose ($M_w$ 1,000,000) and then dissolving it in the mixture solution. The sodium bicarbonate buffer solution was prepared by using 0.05 M of sodium bicarbonate and 0.1 M of sodium hydroxide.

In TABLE 4 are shown the skin penetration rates of the prepared transdermal compositions determined using cadaver skin as mentioned above and the Primary Irritation Indices (P.I.I.) determined by the degree of skin irritation caused by the transdermal compositions.

TABLE 4

| Classification | Example 4 | Example 5 | Comparative Examples 4 |
|---|---|---|---|
| Antivomiting agent* (wt %) Tropisetron hydrochloride salt | 3 | 3 | 3 |
| Ingredients of vehicle (wt %) | | | |
| Ethanol | 20 | 20 | 20 |
| Propylene glycol | 15 | 15 | 15 |
| Sodium bicarbonate buffer solution (pH 9.6) | — | — | 61 |
| Sodium bicarbonate buffer solution (pH 10.0) | 61 | — | — |
| Sodium bicarbonate buffer solution (pH 11.0) | — | 61 | — |
| Glycerol monolaurate | 1 | 1 | 1 |
| Diethyl toluamide | 3 | 3 | 3 |
| Hydroxypropyl cellulose* | 4.3 | 4.3 | 4.3 |
| pH of transdermal composition | 8.0 | 8.3 | 7.8 |

TABLE 4-continued

| Classification | Example 4 | Example 5 | Comparative Examples 4 |
|---|---|---|---|
| Skin penetration rate of antivomiting agent (μg/cm2/h) | 53.3 | 62.5 | 46.0 |
| Degree of skin irritation (P.I.I.) | 0.8 | 0.9 | 0.8 |

*wt % with reference to 100 wt % of the vehicle

As shown in TABLE 4, the transdermal compositions of the present invention employing a sodium bicarbonate buffer solution with a pH ranging from 8 to 9 showed superior skin penetration rates and a low degree of skin irritation. Moreover, the skin penetration rate increased with increases in the pH of the sodium bicarbonate buffer solution.

EXAMPLES 6-8 AND COMPARATIVE EXAMPLES 5-6

A transdermal composition of an antivomiting agent comprising such ingredients as shown in TABLE 5 was made by dissolving the tropisetron hydrochloride salt in a mixed solution consisting of anhydrous ethanol, propylene glycol, a borate buffer solution, glycerol monolaurate, diethyl toluamide followed by further addition of hydroxypropyl cellulose ($M_w$ 1,000,000) and then dissolving it in the mixture solution.

In TABLE 5 are shown the skin penetration rates of the prepared transdermal compositions determined using cadaver skin as mentioned above and the Primary Irritation Indices (P.I.I.) determined by the degree of skin irritation caused by the transdermal compositions.

TABLE 5

| | Examples | | | Comparative Examples | |
|---|---|---|---|---|---|
| Classification | 6 | 7 | 8 | 5 | 6 |
| Antivomiting agent* (wt %) Tropisetron hydrochloride salt | 3 | 3 | 3 | 3 | 3 |
| Ingredients of vehicle (wt %) | | | | | |
| Ethanol | 20 | 20 | 20 | 20 | 20 |
| Propylene glycol | 15 | 15 | 15 | 15 | 15 |
| Borate buffer solution (pH 10.0) | 61.5 | 61 | 60.5 | 60 | 59- |
| Glycerol monolaurate | 0.5 | 1 | 1.5 | 2 | 3 |
| Diethyl toluamide | 3 | 3 | 3 | 3 | 3 |
| Hydroxypropyl cellulose* | 4.3 | 4.3 | 4.3 | 4.3 | 4.3 |
| pH of transdermal composition | 8.2 | 8.2 | 8.2 | 8.2 | 8.2 |
| Skin penetration rate of antivomiting agent (μg/cm²/h) | 38.4 | 54.6 | 64.2 | 70.9 | 82.6 |
| Degree of skin irritation (P.I.I.) | 0.1 | 0.4 | 1.8 | 2.5 | 3.2 |

*wt % with reference to 100 wt % of the vehicle

As shown in TABLE 5, the degree of skin irritation as well as the skin penetration rate increased with an increase in the content of the glycerol monolaurate. Therefore, in order to maintain a low degree of skin irritation, i.e. to keep the P.I.I below 2, the content of glycerol monolaurate could not be higher than 1.5 wt %.

EXAMPLE 9-10 AND COMPARATIVE EXAMPLE 7

A transdermal composition of an antivomiting agent comprising such ingredients as shown in TABLE 6 was made by dissolving the tropisetron hydrochloride salt in a mixed solution consisting of anhydrous ethanol, propylene glycol, a borate buffer solution, glycerol monolaurate, diethyl toluamide followed by further addition of hydroxypropyl cellulose ($M_w$ 1,000,000) and then dissolving it in the mixture solution. In TABLE 6 are shown the skin penetration rates of the prepared transdermal compositions determined using cadaver skin as mentioned above and the Primary Irritation Indices (P.I.I.) determined by the degree of skin irritation caused by the transdermal compositions.

TABLE 6

| | Examples | | | Comparative Example 7 |
|---|---|---|---|---|
| Classification | 9 | 2 | 10 | |
| Antivomiting agent* (wt %) Tropisetron hydrochloride salt | 2 | 3 | 4 | 5 |
| Ingredients of vehicle (wt %) | | | | |
| Ethanol | 20 | 20 | 20 | 20 |
| Propylene glycol | 15 | 15 | 15 | 15 |
| Borate buffer solution (pH 10.0) | 61 | 61 | 61 | 61 |
| Glycerol monolaurate | 1 | 1 | 1 | 1 |
| Diethyl toluamide | 3 | 3 | 3 | 3 |
| Hydroxypropyl cellulose* | 4.3 | 4.3 | 4.3 | 4.3 |
| pH of transdermal composition | 8.3 | 8.2 | 8.2 | 8.1 |
| Skin penetration rate of antivomiting agent (μg/cm²/h) | 28.0 | 54.6 | 63.2 | 85.4 |
| Degree of skin irritation (P.I.I.) | 0.2 | 0.4 | 1.2 | 2.8 |

*wt % with reference to 100 wt % of the vehicle

As shown in TABLE 6, the degree of skin irritation as well as the skin penetration rate increased with an increase in content of the tropisetron hydrochloride salt. Therefore, in order to maintain a low degree of skin irritation, i.e. to keep the P.I.I. below 2, the content of the tropisetron hydrochloride salt could not be higher than 4 wt %.

COMPARATIVE EXAMPLES 8-9

A transdermal composition of an antivomiting agent comprising such ingredients as shown in TABLE 7 was made by dissolving a tropisetron hydrochloride salt in a mixed solution consisting of anhydrous ethanol, propylene glycol, a borate buffer solution, glycerol monolaurate, and diethyl toluamide followed by further addition of hydroxypropyl cellulose ($M_w$ 1,000,000), polyvinyl pyrrolidone or a carbomer and then totally dissolving them in the mixture solution.

In TABLE 7 are shown the skin penetration rates of the prepared transdermal compositions determined using cadaver skin as mentioned above and the Primary Irritation Indices (P.I.I.) determined by the degree of skin irritation caused by the transdermal compositions.

TABLE 7

| | Examples | | Comparative Examples | |
|---|---|---|---|---|
| Classification | 1 | 2 | 8 | 9 |
| Antivomiting agent* (wt %) Tropisetron hydrochloride salt | 3 | 3 | 3 | 3 |

TABLE 7-continued

| | Examples | | Comparative Examples | |
|---|---|---|---|---|
| Classification | 1 | 2 | 8 | 9 |
| Ingredients of vehicle (wt %) | | | | |
| Ethanol | 20 | 20 | 20 | 20 |
| Propylene glycol | 15 | 15 | 15 | 15 |
| Borate buffer solution (pH 10.0) | 61 | 61 | 61 | 61 |
| Glycerol monolaurate | 1 | 1 | 1 | 1 |
| Diethyl toluamide | 3 | 3 | 3 | 3 |
| Hydroxypropyl cellulose* | — | 4.3 | — | — |
| Polyvinyl pyrrolidone* | — | — | 8.0 | — |
| Carbomer* | — | — | — | 2.0 |
| pH of transdermal composition | 8.2 | 8.2 | 8.2 | 8.2 |
| Skin penetration rate of antivomiting agent (μg/cm2/h) | 56.4 | 54.6 | 30.8 | 19.4 |
| Degree of skin irritation (P.I.I.) | — | 0.4 | 0.4 | 0.5 |

*wt % with reference to 100 wt % of the vehicle

As shown in TABLE 7, there was little difference in the skin penetration rate between Examples 1 and 2 and thus it was shown that hydroxypropyl cellulose when used as a thickener did not affect the skin penetration rate of the antivomiting agent. However, the skin penetration rate was remarkably decreased if polyvinyl pyrrolidone or a carbomer was used as the thickener.

COMPARATIVE EXAMPLES 10-11

A transdermal composition of an antivomiting agent comprising such ingredients as shown in TABLE 8 was made by dissolving the tropisetron hydrochloride salt in a mixed solution consisting of anhydrous ethanol, propylene glycol, a water or buffer solution, glycerol monolaurate, and diethyl toluamide followed by further addition of hydroxypropyl cellulose ($M_w$ 1,000,000) and then dissolving it in the mixture solution.

In TABLE 8 are shown the skin penetration rates of the prepared transdermal compositions determined using cadaver skin as mentioned above and the Primary Irritation Indices (P.I.I.) determined by the degree of skin irritation caused by the transdermal compositions.

TABLE 8

| Classification | Example 2 | Comparative Example 10 | Comparative Example 11 |
|---|---|---|---|
| Antivomiting agent* (wt %) Tropisetron hydrochloride salt Ingredients of vehicle (wt %) | 3 | 3 | 3 |
| Ethanol | 20 | 20 | 20 |
| Propylene glycol | 15 | 15 | 15 |
| Water | — | 61 | — |
| Phosphate buffer solution (pH 10.0) | — | — | 61 |
| Borate buffer solution (pH 10.0) | 61 | — | — |
| Glycerol monolaurate | 1 | 1 | 1 |
| Diethyl toluamide | 3 | 3 | 3 |
| Hydroxypropyl cellulose* | 4.3 | 4.3 | 4.3 |
| pH of transdermal composition | 8.2 | 4.9 | 7.2 |
| Skin penetration rate of antivomiting agent (μg/cm2/h) | 54.6 | 20.1 | 21.4 |
| Degree of skin irritation (P.I.I.) | 0.4 | 0.4 | 0.5 |

*wt % with reference to 100 wt % of the vehicle

As shown in TABLE 8, the skin penetration rate of the antivomiting agent was not substantially affected by the use of water or a phosphoric acid buffer solution, while the use of borate buffer solution significantly increased the skin penetration rate. Moreover, in the three cases above, the degrees of skin irritation (P.I.I.) were all in a range of 0.4 to 0.5.

COMPARATIVE EXAMPLE 12-13

A transdermal composition of an antivomiting agent comprising such ingredients as shown in TABLE 9 was formed by dissolving the tropisetron hydrochloride salt in a mixed solution consisting of anhydrous ethanol, propylene glycol, a TRIS buffer solution, glycerol monolaurate, diethyl toluamide followed by further addition of hydroxypropyl cellulose ($M_w$ 1,000,000) and then totally dissolving it in the mixture solution. The TRIS buffer solution was prepared by using 0.1 M of tris(hydroxymethyl)aminomethane and 0.1 M of hydrochloric acid.

In TABLE 9 are shown the skin penetration rates of the prepared transdermal compositions determined by using cadaver skin as mentioned above and the Primary Irritation Indices (P.I.I.) determined by the degree of the skin irritation caused by the transdermal compositions.

TABLE 9

| Classification | Comparative Example 12 | Comparative Example 13 |
|---|---|---|
| Antivomiting agent* (wt %) Tropisetron hydrochloride salt Ingredients of vehicle (wt %) | 3 | 3 |
| Ethanol | 20 | 20 |
| Propylene glycol | 15 | 15 |
| TRIS buffer solution (pH 8.5) | — | 61 |
| TRIS buffer solution (pH 9.5) | 61 | — |
| Glycerol monolaurate | 1 | 1 |
| Diethyl toluamide | 3 | 3 |
| Hydroxypropyl cellulose* | 4.3 | 4.3 |
| pH of transdermal composition | 8.2 | 7.9 |
| Skin penetration rate of antivomiting agent (μg/cm²/h) | 52.2 | 48.2 |
| Degree of skin irritation (P.I.I.) | 2.0 | 1.5 |

*wt % with reference to 100 wt % of the vehicle

As shown in TABLE 9, the transdermal compositions employing a TRIS buffer solution with a pH ranging from 8 to 9 showed a high degree of skin irritation.

COMPARATIVE EXAMPLE 14-15

A transdermal composition of an antivomiting agent comprising such ingredients as shown in TABLE 10 was made by dissolving the tropisetron hydrochloride salt in a mixed solution consisting of anhydrous ethanol, propylene glycol, an ammonia buffer solution, glycerol monolaurate, diethyl toluamide followed by further addition of hydroxypropyl cellulose ($M_w$ 1,000,000) and then dissolving it in the mixture solution. The ammonia buffer solution was prepared by using 2 M of ammonia and 2 M of ammonium chloride.

In TABLE 10 are shown the skin penetration rates of the prepared transdermal compositions determined using cadaver skin as mentioned above and the Primary Irritation Indices (P.I.I.) determined by the degree of skin irritation caused by the transdermal compositions.

TABLE 10

| Classification | Comparative Example 14 | Comparative Example 15 |
|---|---|---|
| Antivomiting agent* (wt %) Tropisetron hydrochloride salt | 3 | 3 |
| Ingredients of vehicle (wt %) | | |
| Ethanol | 20 | 20 |
| Propylene glycol | 15 | 15 |
| Ammonia buffer solution (pH 9.1) | 61 | — |
| Ammonia buffer solution (pH 10.4) | — | 61 |
| Glycerol monolaurate | 1 | 1 |
| Diethyl toluamide | 3 | 3 |
| Hydroxypropyl cellulose* | 4.3 | 4.3 |
| pH of transdermal composition | 8.3 | 8.6 |
| Skin penetration rate of antivomiting agent ($\mu g/cm^2/h$) | 52.1 | 50.6 |
| Degree of skin irritation (P.I.I.) | 1.3 | 2.0 |

*wt % with reference to 100 wt % of the vehicle

As shown in TABLE 10, the transdermal compositions employing an ammonia buffer solution of with a pH ranging from 8 to 9 showed a high degree of skin irritation.

As described above, the transdermal composition of the present invention has the effect of enhancing the skin penetration rate as well as lowering the degree of skin irritation caused. Moreover, the transdermal composition of the present invention is adequately viscous and has a superior skin penetration rate and therefore is particularly suitable to be used in the form of a patch.

It is to be understood that the above-referenced arrangements are illustrative of application of the principles of the present invention. While the present invention has been shown and described above in connection with the exemplary embodiments(s) of the invention, numerous modifications and alternative arrangements can be devised without departing from the spirit and scope of the present invention. It will be apparent to those of ordinary skill in the art that numerous modifications can be made without departing from the principles and concepts of the invention as set forth in the claims.

What is claimed is:

1. A transdermal composition of an antivomiting agent comprising:
    (a) 96 to 98 wt % of a vehicle for transdermal delivery comprising
        (i) 25 to 45 wt % of a mixed solution comprising ethanol and propylene glycol,
        (ii) a skin penetration enhancer containing 0.5 to 1.5 wt % of a fatty acid ester, and 2 to 5 wt % of an amide compound,
        (iii) 50 to 70 wt % of a borate buffer solution; and
    (b) 2 to 4 wt % of a pharmaceutically acceptable salt of tropisetron as an antivomiting agent, wherein the pH of said composition is within the range of 8 to 9.

2. The transdermal composition according to claim 1, wherein said transdermal composition has a pH in the range of 8 to 8.5.

3. The transdermal composition according to claim 1, wherein said fatty acid ester is present in an amount of 1 to 1.5 wt %.

4. The transdermal composition according to claim 1, wherein said tropisetron is present in an amount of 2.5 to 3.5 wt %.

5. The transdermal composition according to claim 1, wherein said tropisetron is in the form of its hydrochloride salt.

6. The transdermal composition according to claim 1, wherein said fatty acid ester is selected from the group consisting of glycerol monolaurate, glycerol monooleate, glycerol monolinoleate, glycerol trilaurate, glycerol trioleate, glycerol tricaprylate, propylene glycol monolaurate, propylene glycol dilaurate, caprylic/capric triglyceride, methyl laurate, methyl caprate, isopropyl myristate, isopropyl palmitate, ethyl oleate and oleyl oleate.

7. The transdermal composition according to claim 6, wherein said fatty acid ester is glycerol monolaurate.

8. The transdermal composition according to claim 1, wherein said amide compound is selected from the group consisting of N,N-diethyl-m-toluamide, lauric acid diethanolamide, urea, dimethylformamide and dimethylacetamide.

9. The transdermal composition according to claim 8, wherein said amide compound is N,N-diethyl-m-toluamide.

10. The transdermal composition according to claim 1, wherein said composition further comprises a thickener present in the amount of 4 to 5 wt % with reference to 100 wt % of said vehicle.

11. The transdermal composition according to claim 10, wherein said thickener is hydroxypropyl cellulose with a weight average molecular weight of 800,000 to 1,000,000.

12. A method of transdermally delivering an antivomiting agent to a warm blooded animal comprising administering a transdermal delivering device containing a composition comprising:
    (a) a vehicle for transdermal delivery comprising
        (i) 25 to 45 wt % of a mixed solution comprising ethanol and propylene glycol,
        (ii) a skin penetration enhancer containing 0.5 to 1.5 wt % of a fatty acid ester, and 2 to 5 wt % of an amide compound,
        (iii) 50 to 70 wt % of a borate buffer solution; and
    (b) 2 to 4 wt %, based on the weight of vehicle, a pharmaceutically acceptable salt of tropisetron as an antivomiting agent, wherein the pH of said composition is within the range of 8 to 9.

13. The method according to claim 12, wherein said composition has a pH in the range of 8 to 8.5.

14. The transdermal composition according to claim 12, wherein said fatty acid ester is present in an amount of 1 to 1.5 wt %.

15. The method according to claim 12, wherein said tropisetron is present in an amount of 2.5 to 3.5 wt %.

16. The method according to claim 12, wherein said tropisetron is in the form of its hydrochloride salt.

17. The method according to claim 12, wherein said fatty acid ester is selected from the group consisting of glycerol monolaurate, glycerol monooleate, glycerol monolinoleate, glycerol trilaurate, glycerol trioleate, glycerol tricaprylate, propylene glycol monolaurate, propylene glycol dilaurate, caprylic/capric triglyceride, methyl laurate, methyl caprate, isopropyl myristate, isopropyl palmitate, ethyl oleate and oleyl oleate.

18. The method according to claim 17, wherein said fatty acid ester is glycerol monolaurate.

19. The method according to claim 12, wherein said amide compound is selected from the group consisting of N,N-diethyl-m-toluamide, lauric acid diethanolamide, urea, dimethylformamide and dimethylacetamide.

20. The method according to claim 19, wherein said amide compound is N,N-diethyl-m-toluamide.

21. The method according to claim 12, wherein said composition further comprises a thickener presented in the amount of 4 to 5 wt % with reference to 100 wt % of said vehicle.

22. The method according to claim 21, wherein said thickener is hydroxypropyl cellulose with a weight average molecular weight of 800,000 to 1,000,000.

* * * * *